(12) United States Patent
Kodate

(10) Patent No.: US 8,592,532 B2
(45) Date of Patent: Nov. 26, 2013

(54) METHOD FOR PRODUCING ORGANOPOLYSILOXANE COMPOUND

(75) Inventor: Takashi Kodate, Wakayama (JP)

(73) Assignee: KAO Corporation, Tokyo (JP)

( * ) Notice: Subject to any disclaimer, the term of this patent is extended or adjusted under 35 U.S.C. 154(b) by 0 days.

(21) Appl. No.: 13/639,313

(22) PCT Filed: Apr. 4, 2011

(86) PCT No.: PCT/JP2011/058560
§ 371 (c)(1),
(2), (4) Date: Oct. 4, 2012

(87) PCT Pub. No.: WO2011/125989
PCT Pub. Date: Oct. 13, 2011

(65) Prior Publication Data
US 2013/0030138 A1    Jan. 31, 2013

(30) Foreign Application Priority Data
Apr. 7, 2010    (JP) ................. 2010-088587

(51) Int. Cl.
*C08F 283/12*    (2006.01)
*C08G 77/388*   (2006.01)
*C08L 83/08*    (2006.01)

(52) U.S. Cl.
USPC ................. 525/474; 528/423; 528/424

(58) Field of Classification Search
USPC .................. 525/474; 528/423, 424
See application file for complete search history.

(56) References Cited

U.S. PATENT DOCUMENTS

| | | | |
|---|---|---|---|
| 5,171,821 A * | 12/1992 | Nozawa et al. ............... | 528/125 |
| 5,472,689 A * | 12/1995 | Ito ............................ | 424/70.122 |
| 5,747,016 A * | 5/1998 | Yui et al. ................... | 424/401 |
| 6,027,718 A | 2/2000 | Takiguchi et al. | |
| 6,610,278 B2 * | 8/2003 | Kashimoto ................ | 424/64 |
| 7,001,864 B2 * | 2/2006 | Kiso et al. ................. | 502/155 |
| 2004/0192875 A1 * | 9/2004 | Kiso et al. ................. | 528/48 |
| 2006/0045862 A1 * | 3/2006 | Tada et al. ................. | 424/70.122 |
| 2010/0203002 A1 | 8/2010 | Fukuhara et al. | |
| 2012/0220723 A1 | 8/2012 | Fukuhara et al. | |
| 2013/0030138 A1 * | 1/2013 | Kodate ......................... | 528/28 |

FOREIGN PATENT DOCUMENTS

| | | |
|---|---|---|
| EP | 0 290 109 A2 | 11/1988 |
| JP | 2 276824 | 11/1990 |
| JP | 4 85335 | 3/1992 |
| JP | 10 279690 | 10/1998 |
| JP | 10 306163 | 11/1998 |
| JP | 2009 256367 | 11/2009 |
| WO | 2009 014237 | 1/2009 |

OTHER PUBLICATIONS

International Search Report Issued Jun. 7, 2011 in PCT/JP11/58560 Filed Apr. 4, 2011.
Supplementary European Search Report issued Sep. 20, 2013, in European Patent Application No. 11765889.8 (with English-language Translation).

* cited by examiner

*Primary Examiner* — Mike M Dollinger
(74) *Attorney, Agent, or Firm* — Oblon, Spivak, McClelland, Maier & Neustadt, L.L.P.

(57) ABSTRACT

The present invention relates to a method for producing an organopolysiloxane compound having a structure in which a poly(N-acylalkylene imine) segment containing a repeating unit represented by the following general formula (1) is bonded to a terminal end and/or a side chain of an organopolysiloxane segment, the method including the steps of (a) subjecting a cyclic iminoether compound represented by the following general formula (I) to ring opening polymerization in a solvent to prepare a solution of a terminal-reactive poly(N-acylalkylene imine); (b) mixing a modified organopolysiloxane containing an amino group bonded to a terminal end and/or a side chain of a molecular chain thereof with a solvent to prepare a solution of the modified organopolysiloxane; (c) mixing the terminal-reactive poly(N-acylalkylene imine) solution prepared in the step (a) with the modified organopolysiloxane solution prepared in the step (b) to react the amino group contained in the modified organopolysiloxane with the terminal-reactive poly(N-acylalkylene imine); (d) adding a basic substance to a reaction product obtained in the step (c); and (e) removing the solvents from a mixture obtained after the addition in the step (d) at a temperature of from 100 to 200° C.:

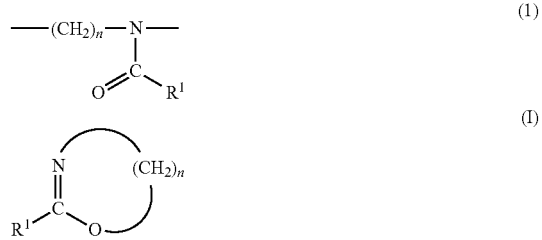

wherein $R^1$ is a hydrogen atom, an alkyl group having 1 to 22 carbon atoms, an aralkyl group or an aryl group; and n is a number of 2 or 3.

15 Claims, No Drawings

METHOD FOR PRODUCING ORGANOPOLYSILOXANE COMPOUND

CROSS REFERENCE TO RELATED APPLICATION

This application is a 371 of PCT/JP2011/058560, filed on Apr. 4, 2011, and claims priority to Japanese Patent Application No. 2010-088587, filed on Apr. 7, 2010.

TECHNICAL FIELD

The present invention relates to a method for producing organopolysiloxane compounds.

BACKGROUND ART

Organopolysiloxane compounds (hereinafter also referred to as "silicone compounds") have various characteristics, such as low surface tension, good lubricating properties and mold releasability, high heat stability, glass transition point generally extremely low, and good gas permeability. With these characteristics, various forms of silicone compounds have been used in an extremely wide range of applications, for example, as lubricants, heat media, electrical insulators, leveling agents for paints, mold release agents, cosmetic additives, fiber treating agents, shock absorbers, sealing materials, templating agents, glazing agents, foam stabilizers, and defoaming agents.

Also in the field of personal care, silicone compounds have been widely used, for example, to improve the texture of cosmetics, such as skin care products, foundations, shampoos, and conditioners. Silicone compounds have been also used as a base material of hair setting agents. Many customers desire personal care products having texture with little sticky nature in a solid state. In addition, silicone compounds are required to be soluble in ethanol in view of easiness of blending. For example, Patent Document 1 discloses a silicone compound which is soluble or dispersible in various solvents, such as ethanol.

CITATION LIST

Patent Literature

[Patent Document 1]: JP 2-276824A
[Patent Document 2]: JP 4-85335A

SUMMARY OF INVENTION

Technical Problem

As described, for example, in Patent Document 2, there is known a method for producing a silicone elastomer which is a two-stage process including a step of polymerizing a poly (N-acylalkylene imine) oligomer and grafting the resulting oligomer to a silicone compound. In these steps, it is required to conduct the reactions in a homogeneous system. For this reason, these reactions are generally carried out in a solvent such as ethyl acetate and chloroform.

In the case where the silicone compounds produced by the above method are used in the personal care product applications, it has been required to provide a step of removing the solvent used therein after completion of the reaction. In particular, the solvent odor is undesirable in the personal care product applications. Therefore, in personal care product applications, it has been required to remove the residual solvents from the reaction solution and reduce them to as small a level as possible. For this purpose, the removal of solvent must be carried out at a high temperature under reduced pressure.

The silicone compounds described in Patent Document 1 have an excellent solubility in various solvents which is not attainable in conventionally available products. However, the silicone compounds have failed to ensure a stable quality upon production thereof. In particular, when the solvent removal treatment or the like is conducted in high-temperature conditions, the molecular weight of the resulting silicone compounds tends to be reduced, so that a touch thereof tends to be deteriorated.

The present invention relates to a method for producing an organopolysiloxane compound having a stable quality without reduction in molecular weight thereof.

Solution to Problem

That is, the present invention relates to a method for producing an organopolysiloxane compound having a structure in which a poly(N-acylalkylene imine) segment containing a repeating unit represented by general formula (1):

wherein $R^1$ is a hydrogen atom, an alkyl group having 1 to 22 carbon atoms, an aralkyl group or an aryl group; and n is a number of 2 or 3,
is bonded to a terminal end and/or a side chain of an organopolysiloxane segment,
the method comprising the steps of:
(a) subjecting a cyclic iminoether compound represented by general formula (I):

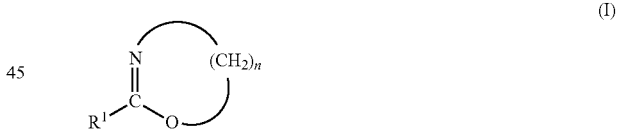

wherein $R^1$ and n are the same as those defined in the general formula (1):
to ring opening polymerization in a solvent to prepare a solution of a terminal-reactive poly(N-acylalkylene imine);
(b) mixing a modified organopolysiloxane containing an amino group bonded to a terminal end and/or a side chain of a molecular chain thereof with a solvent to prepare a solution of the modified organopolysiloxane;
(c) mixing the terminal-reactive poly(N-acylalkylene imine) solution prepared in the step (a) with the modified organopolysiloxane solution prepared in the step (b) to react the amino group contained in the modified organopolysiloxane with the terminal-reactive poly(N-acylalkylene imine);
(d) adding a basic substance to a reaction product obtained in the step (c); and
(e) removing the solvents from a mixture obtained after the addition in the step (d) at a temperature of from 100 to 200° C.

Advantageous Effects of Invention

According to the method of the present invention, it is possible to produce an organopolysiloxane compound having a good touch without stickiness and a stable quality while suppressing reduction in molecular weight thereof.

DESCRIPTION OF EMBODIMENTS

<Organopolysiloxane Compound>

The organopolysiloxane compound produced by the method of the present invention has a structure in which a poly(N-acylalkylene imine) segment containing a repeating unit represented by the following general formula (1) is bonded to a terminal end and/or a side chain of an organopolysiloxane segment.

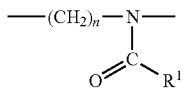
(1)

In the general formula (1), $R^1$ is a hydrogen atom, an alkyl group having 1 to 22 carbon atoms, an aralkyl group or an aryl group; and n is a number of 2 or 3.

The organopolysiloxane compound is not particularly limited. Specific examples of the preferred organopolysiloxane compound include those compounds each constituted from a modified organopolysiloxane segment represented by the following general formula (2), and the poly(N-acylalkylene imine) segment containing a repeating unit represented by the general formula (1).

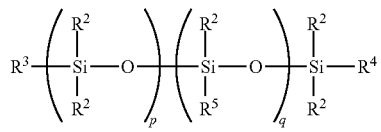
(2)

In the general formula (2), a plurality of $R^2$ groups are each independently an alkyl group having 1 to 22 carbon atoms or a phenyl group; $R^3$ and $R^4$ are each independently an alkyl group having 1 to 22 carbon atoms, a phenyl group or a divalent bonding group represented by any of the following formulae (i) to (vi); $R^5$ is a divalent bonding group represented by any of the following formulae (i) to (vi); p is an integer of 2 to 4,000; and q is an integer of 2 to 250.

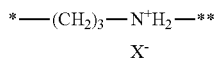
(i)

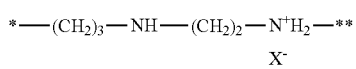
(ii)

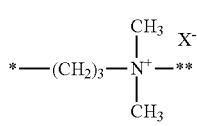
(iii)

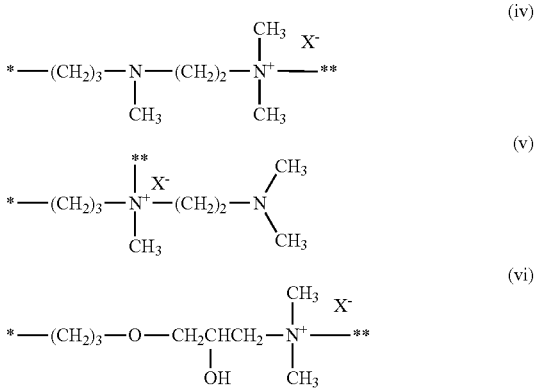

In the formulae (i) to (vi), * represents a site to be bonded to a silicon atom in the general formula (2); ** represents a site to be bonded to the poly(N-acylalkylene imine) segment containing a repeating unit represented by the general formula (1); and $X^-$ represents a counter ion of an ammonium ion.

The alkyl group having 1 to 22 carbon atoms which is represented by $R^1$ in the general formula (1) is preferably a linear, branched or cyclic alkyl group having 1 to 22 carbon atoms, more preferably a linear, branched or cyclic alkyl group having 1 to 10 carbon atoms, and still more preferably a linear, branched or cyclic alkyl group having 1 to 6 carbon atoms. Specific example of the alkyl group having 1 to 22 carbon atoms which is represented by $R^1$ include a methyl group, an ethyl group, an n-propyl group, an isopropyl group, an n-butyl group, an isobutyl group, a sec-butyl group, a tert-butyl group, various pentyl groups, various hexyl groups, various heptyl groups, various octyl groups, various nonyl groups, various decyl groups, various undecyl groups, various dodecyl groups, various octadecyl groups, various nonadecyl groups, various eicosyl groups, various docosyl groups, a cyclopentyl group and a cyclohexyl group. Meanwhile, the various alkyl groups as used herein mean to include all isomers as the alkyl groups having the same carbon number.

The aralkyl group represented by $R^1$ in the general formula (1) is preferably an aralkyl group having 7 to 15 carbon atoms, more preferably an aralkyl group having 7 to 14 carbon atoms and still more preferably an aralkyl group having 7 to 10 carbon atoms. Specific examples of the aralkyl group represented by $R^1$ in the general formula (1) include a benzyl group, a phenethyl group, a 3-phenyl propyl group, a trityl group, a naphthyl methyl group and an anthryl methyl group. Meanwhile, in the aralkyl group, a lower alkyl group may be introduced onto an aromatic ring thereof.

The aryl group represented by $R^1$ in the general formula (1) is preferably an aryl group having 6 to 14 carbon atoms, more preferably an aryl group having 6 to 12 carbon atoms and still more preferably an aryl group having 6 to 9 carbon atoms. Specific examples of the aryl group represented by $R^1$ include a phenyl group, a tolyl group, a xylyl group, a naphthyl group, a biphenyl group, an anthryl group and a phenanthryl group.

Among these groups as $R^1$, preferred are linear or branched alkyl groups having 1 to 6 carbon atoms, more preferred are linear or branched alkyl groups having 1 to 3 carbon atoms, and especially preferred is an ethyl group.

In the general formula (1), n is preferably 2.

The alkyl group having 1 to 22 carbon atoms represented by $R^2$ to $R^4$ in the general formula (2) means the same alkyl group having 1 to 22 carbon atoms as represented by $R^1$ in the general formula (1), and the preferred ranges thereof are also the same as described above.

The alkyl group having 1 to 22 carbon atoms represented by $R^2$ is preferably a linear or branched alkyl group having 1 to 6 carbon atoms, more preferably a linear or branched alkyl group having 1 to 3 carbon atoms, and especially preferably a methyl group. In addition, when $R^3$ and $R^4$ respectively represent an alkyl group having 1 to 22 carbon atoms or a phenyl group, $R^3$ and $R^4$ are also respectively preferably a linear or branched alkyl group having 1 to 6 carbon atoms, more preferably a linear or branched alkyl group having 1 to 3 carbon atoms, and especially preferably a methyl group.

The divalent bonding group represented by any of the formulae (i) to (vi) as $R^3$ to $R^5$ in the general formula (2) is an alkylene group containing a nitrogen atom which functions as a bonding group for bonding the modified organopolysiloxane segment and the poly(N-acylalkylene imine) segment. Among the bonding groups represented by the formulae (i) to (vi), preferred are those groups represented by the formulae (i) and (ii).

In the formulae (i) to (vi), $X^-$ represents a counter ion of an ammonium ion. Specific examples of the counter ion of an ammonium ion represented by $X^-$ include an ethyl sulfuric acid ion, a methyl sulfuric acid ion, a chlorine ion, an iodine ion, a ½ sulfuric acid ion, a p-toluene sulfonic acid ion and a perchloric acid ion.

In the general formula (2), p represents an integer of from 2 to 4000, and q represents an integer of from 2 to 150. Further, p is preferably an integer of from 135 to 1600 and more preferably an integer of from 400 to 1350, and q is preferably an integer of from 2 to 50, more preferably an integer of from 5 to 30, still more preferably an integer of from 10 to 25, and further still more preferably an integer of from 15 to 25.

The bonding rate of the organopolysiloxane segment as used in the present specification means a proportion of amino groups in the modified organopolysiloxane segment to which the poly(N-acylalkylene imine) segment is bonded, on the basis of whole amino groups contained in the modified organopolysiloxane segment. The bonding rate of the organopolysiloxane segment is calculated from the following calculation formula (1) by subjecting the organopolysiloxane compound to neutralization titration to measure a content of the unreacted amino groups therein.

Bonding Rate (%)=([1−Content (mol/g) of Unreacted Amino Groups]/(Content (mol/g) of Whole Amino Groups Contained in Modified Organopolysiloxane Segment)×100   (1)

The effects of the present invention are more remarkably exhibited when the bonding rate of the organopolysiloxane segment is high. From this viewpoint, the bonding rate of the organopolysiloxane segment is preferably from 80 to 100%, more preferably from 90 to 100%, still more preferably from 95 to 100% and especially from 97 to 100%.

The molecular weight of the poly(N-acylalkylene imine) segment in the organopolysiloxane compound may be calculated from a molecular weight of an N-acylalkylene imine unit and a polymerization degree thereof measured by NMR, etc., or may be measured by gel permeation chromatography (GPC). The molecular weight as used herein means a number-average molecular weight ($MN_{OX}$) as measured in terms of polystyrene as a reference standard substance by GPC. From the viewpoints of a good touch and a good solubility in ethanol when using the resulting organopolysiloxane compound in cosmetic applications, $MN_{OX}$ is preferably from 150 to 50,000, more preferably from 500 to 10,000, still more preferably from 800 to 5,000, and especially preferably from 1,000 to 3,000. The weight-average molecular weight of the poly(N-acylalkylene imine) segment in the organopolysiloxane compound as measured in terms of polystyrene as a reference standard substance by GPC is preferably from 180 to 65,000, more preferably from 600 to 13,000, still more preferably from 960 to 6,500, further still more preferably from 1,200 to 3,900, and especially preferably from 1,200 to 2,000.

The details of specific measurement conditions of the GPC are shown in Examples below.

The weight-average molecular weight ($MW_{Si}$) of the organopolysiloxane segment constituting a main chain of the organopolysiloxane compound is preferably from 300 to 300,000. From the viewpoint of a good solubility in ethanol, the weight-average molecular weight ($MW_{Si}$) is more preferably from 10,000 to 120,000 and still more preferably from 30,000 to 100,000. Since the organopolysiloxane compound has a skeleton common to the modified organopolysiloxane as a raw material compound thereof, the $MW_{Si}$ is substantially the same as the weight-average molecular weight of the modified organopolysiloxane. Meanwhile, the weight-average molecular weight of the modified organopolysiloxane as used herein means a weight-average molecular weight in terms of polystyrene as a reference standard substance as measured by previously acetylating active hydrogen therein with acetic anhydride and then subjecting the resulting acetylation product to GPC measurement.

The ratio of a mass (MO of the organopolysiloxane segment to a mass ($M_{SiOX}$) of the organopolysiloxane compound produced by the method of the present invention (hereinafter occasionally referred to merely as a "mass ratio (r) of the organopolysiloxane segment") is preferably from 0.1 to 0.95, more preferably from 0.3 to 0.9 and still more preferably from 0.5 to 0.8 from the viewpoints of a good touch and a good solubility in ethanol when using the resulting organopolysiloxane compound in cosmetic applications. Meanwhile, the mass ratio (r) of the organopolysiloxane segment is defined by the following formula.

$$r = M_{Si}/M_{SiOX} = M_{Si}/(M_{Si}+M_{OX})$$

wherein $M_{Si}$ and $M_{SiOX}$ have the same meanings as defined above, and $M_{OX}$ represents a mass of the poly(N-acylalkylene imine) segment.

The average value of the mass ratio (r) of the organopolysiloxane segment may be calculated from an integral ratio between an alkyl group or a phenyl group in the organopolysiloxane segment and a methylene group in the poly(N-acylalkylene imine) segment which are measured by dissolving the organopolysiloxane compound according to the present invention in deuterated chloroform to prepare a 5% by mass solution thereof and then subjecting the resulting solution to nuclear magnetic resonance ($^1$H-NMR) analysis.

The weight-average molecular weight ($MW_t$) of the organopolysiloxane compound according to the present invention is preferably from 500 to 500,000, more preferably from 30,000 to 150,000 and still more preferably from 50,000 to 120,000. The weight-average molecular weight ($MW_t$) may be determined by GPC measurement described in Examples below.

Specific examples of the organopolysiloxane compound according to the present invention include those compounds described in JP 2-276824A (Patent Document 1), JP 2009-24114A and the like.

<Production Method of Organopolysiloxane Compound>

The organopolysiloxane compound according to the present invention may be produced by reacting a modified organopolysiloxane containing an amino group bonded to a terminal end and/or a side chain of a molecular chain thereof with a terminal-reactive poly(N-acylalkylene imine).

The method the present invention includes the following steps (a) to (e):

(a) subjecting a cyclic iminoether compound represented by general formula (I):

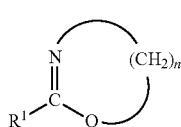

wherein $R^1$ is a hydrogen atom, an alkyl group having 1 to 22 carbon atoms, an aralkyl group or an aryl group; and n is a number of 2 or 3,
to ring opening polymerization in a solvent to prepare a solution of a terminal-reactive poly(N-acylalkylene imine);

(b) mixing a modified organopolysiloxane containing an amino group bonded to a terminal end and/or a side chain of a molecular chain thereof with a solvent to prepare a solution of the modified organopolysiloxane;

(c) mixing the terminal-reactive poly(N-acylalkylene imine) solution prepared in the step (a) with the modified organopolysiloxane solution prepared in the step (b) to react the amino group contained in the modified organopolysiloxane with the terminal-reactive poly(N-acylalkylene imine);

(d) adding a basic substance to a reaction product obtained in the step (c); and (e) removing the solvents from a mixture obtained after the addition in the step (d) at a temperature of from 100 to 200° C.

[Step (a)]

In the step (a), the cyclic iminoether compound represented by the general formula (I) is subjected to ring opening polymerization (living polymerization) in a solvent to prepare a solution of a terminal-reactive poly(N-acylalkylene imine).

$R^1$ and n in the general formula (I) are the same as $R^1$ and n as defined in the general formula (1), and the preferred ranges thereof are also the same as described in the general formula (1).

(Ring Opening Polymerization of Cyclic Iminoether Compound)

The solvent used in the ring opening polymerization of the cyclic iminoether compound is preferably an aprotic polar solvent. Specific examples of the solvent include acetic acid alkyl (C1 to C3) esters such as ethyl acetate and propyl acetate; dialkyl (C1 to C3) ethers such as diethyl ether and diisopropyl ether; cyclic ethers such as dioxane and tetrahydrofuran; ketones such as acetone and methyl ethyl ketone; halogen solvents such as chloroform and methylene chloride; nitrile solvents such as acetonitrile and benzonitrile; and other solvents such as N,N-dimethylformamide, N,N-dimethylacetamide and dimethyl sulfoxide. Among these solvents, acetic acid alkyl (C1 to C3) esters can be more suitably used.

The concentration of water contained in the cyclic iminoether compound solution prepared by mixing the cyclic iminoether compound in the solvent is preferably 600 mg/kg or less, more preferably 200 mg/kg or less and still more preferably 100 mg/kg or less from the viewpoint of well controlling a molecular weight of the resulting polymer. On the other hand, from the viewpoint of a high efficiency of operation, the concentration of water in the cyclic iminoether compound solution is preferably 10 mg/kg or more, more preferably 30 mg/kg or more, still more preferably 50 mg/kg or more, and especially preferably 70 mg/kg or more.

When the amount of water in the cyclic iminoether compound solution is excessively large, the solution is preferably subjected to dehydration and drying treatment. The dehydration and drying treatment is preferably carried out under reduced pressure or using a dehydration agent. From the viewpoint of reducing a burden on facilities, the dehydration and drying treatment is more preferably carried out using a dehydration agent. Examples of the dehydration agent include a molecular sieve, alumina, calcium chloride and calcium sulfate. Among these dehydration agents, preferred is a molecular sieve from the viewpoints of achievability of the water concentration and economy.

From the viewpoint of shortening the dehydration time, the dehydration temperature is preferably 50° C. or lower, more preferably 40° C. or lower and still more preferably 35° C. or lower. Also, from the viewpoint of a high efficiency of operation, the dehydration temperature is preferably 5° C. or higher.

The dehydration agent may be directly added to the cyclic iminoether compound solution, followed by stirring the resulting mixture, and thereafter the dehydration agent may be removed from the mixture. However, from the viewpoint of a facilitated operation, the cyclic iminoether compound solution is preferably dehydrated by passing through a column filled with the dehydration agent. The concentration of the cyclic iminoether compound in the cyclic iminoether compound solution is preferably from 10 to 80% by mass, more preferably from 20 to 60% by mass and still more preferably from 25 to 55% by mass from the viewpoint of shortening the dehydration time.

The ring opening polymerization of the cyclic iminoether compound may be carried out in the presence of a polymerization initiator. As the polymerization initiator, there may be used compounds having a high electrophilic reactivity. Examples of the polymerization initiator include strong acid alkyl esters such as benzene-sulfonic acid alkyl esters, p-toluene-sulfonic acid alkyl esters, trifluoromethane-sulfonic acid alkyl esters, trifluoroacetic acid alkyl esters and sulfuric acid dialkyl esters. Among these polymerization initiators, especially preferred are dialkyl sulfates, in particular, those dialkyl sulfates containing an alkyl group having 1 to 3 carbon atoms because they serve for converting an amino group, preferably a primary amino group, introduced into a terminal end and/or a side chain of a molecular chain of the modified organopolysiloxane used in the below-mentioned step (c), into ammonium ion (whose counter ion is an alkylsulfuric acid ion) to form the bonding group represented by the formula (iv) and contribute to bonding between the terminal-reactive poly(N-acylalkylene imine) and the modified organopolysiloxane. The polymerization initiator may be usually used in an amount of 1 mol on the basis of from 2 to 100 mol of the cyclic iminoether compound.

The polymerization temperature is preferably from 40 to 150° C., more preferably from 60 to 120° C., still more preferably from 70 to 110° C. and further still more preferably from 75 to 100° C. From the viewpoint of well controlling a molecular weight of the resulting polymer, the polymerization temperature is preferably adjusted to the above-specified range after completion of adding the polymerization initiator.

The polymerization time may vary depending upon the polymerization reaction conditions such as polymerization temperature, and is usually from 1 to 60 h, preferably from 2 to 50 h, more preferably from 3 to 30 h and still more preferably from 5 to 15 h.

For example, when using a 2-substituted-2-oxazoline as the cyclic iminoether compound represented by the general formula (I), it is possible to produce a poly(N-acylethylene imine) of the general formula (1) wherein n is 2 (n=2). Also, when using a 2-substituted-dihydro-2-oxazoline as the cyclic iminoether compound represented by the general formula (I), it is possible to produce a poly(N-acylethylene imine) of the general formula (1) wherein n is 3 (n=3).

The number-average molecular weight of the terminal-reactive poly(N-acylalkylene imine) obtained by the ring opening polymerization is preferably from 150 to 50,000, more preferably from 500 to 10,000, still more preferably from 800 to 5,000 and especially preferably from 1,000 to 3,000. The number-average molecular weight of the terminal-reactive poly(N-acylalkylene imine) is preferably 150 or more from the viewpoint of enhancing a solubility in ethanol of the resulting organopolysiloxane compound, and 50,000 or less from the viewpoint of facilitated production thereof.

[Step (b)]

In the step (b), the modified organopolysiloxane containing an amino group bonded to a terminal end and/or a side chain of a molecular chain thereof is mixed with a solvent to prepare a solution of the modified organopolysiloxane.

The modified organopolysiloxane containing an amino group bonded to a terminal end and/or a side chain of a molecular chain thereof is not particularly limited. Specific examples of the preferred modified organopolysiloxane include those modified organopolysiloxanes represented by the following general formula (II).

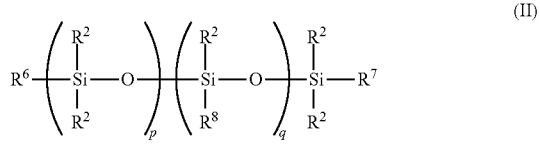

(II)

wherein a plurality of $R^2$ groups are each independently an alkyl group having 1 to 22 carbon atoms or a phenyl group; $R^6$ and $R^7$ are each independently an alkyl group having 1 to 22 carbon atoms or a phenyl group, or a substituent group represented by any of the following formulae (vii) to (xi); $R^8$ is a substituent group represented by any of the following formulae (vii) to (xi); p is an integer of from 2 to 4,000; and q is an integer of from 2 to 150.

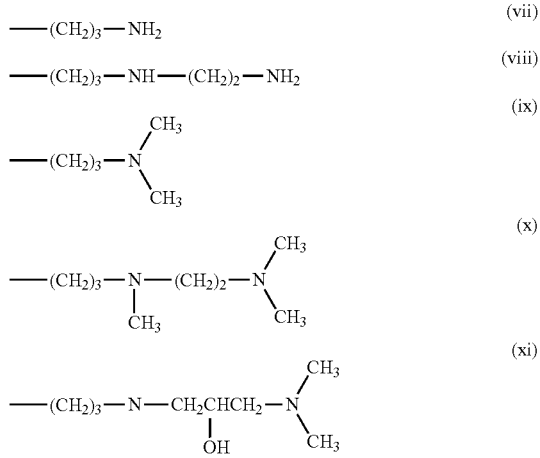

In the general formula (II), the alkyl group having 1 to 22 carbon atoms and the phenyl group which are represented by $R^2$, $R^6$ and $R^7$ are the same as the alkyl group having 1 to 22 carbon atoms and the phenyl group which are represented by $R^2$ to $R^4$ in the general formula (2), and the preferred ranges thereof are also the same as specified with respect to $R^2$ to $R^4$ in the general formula (2). In addition, p and q in the general formula (II) are the same as those in the general formula (2), and the preferred ranges thereof are also the same as those in the general formula (2).

Among the substituent groups represented by any of the formulae (vii) to (xi), preferred are those substituent groups represented by the formula (vii) or (viii).

The modified organopolysiloxane may be produced by any optional methods. In addition, as the modified organopolysiloxane, there may also be used commercially available products. Specific examples of the commercially available products of the modified organopolysiloxane include "KF-8015", "KF-864" and "KF-8003" (tradenames) all available from Shin-Etsu Silicone Co., Ltd., and "BY16-898" (tradename) available from Dow Corning Toray Co., Ltd.

The solvent used in the step (b) is preferably an aprotic polar solvent. Specific examples of the solvent include acetic acid alkyl (C1 to C3) esters such as ethyl acetate and propyl acetate; dialkyl (C1 to C3) ethers such as diethyl ether and diisopropyl ether; cyclic ethers such as dioxane and tetrahydrofuran; ketones such as acetone and methyl ethyl ketone; halogen solvents such as chloroform and methylene chloride; nitrile solvents such as acetonitrile and benzonitrile; and other solvents such as N,N-dimethylformamide, N,N-dimethylacetamide and dimethyl sulfoxide. Among these solvents, acetic acid alkyl (C1 to C3) esters can be more suitably used. From the viewpoints of facilitated separation of the solvent and low product costs, the solvent used in the step (b) is preferably the same solvent as used in the step (a).

The concentration of the modified organopolysiloxane in the solution is preferably controlled to from 10 to 70% by mass, more preferably from 20 to 60% by mass and still more preferably from 30 to 50% by mass from the viewpoint of a high efficiency of the dehydration and drying treatment.

From the viewpoint of a good touch of the organopolysiloxane produced by the method of the present invention, the concentration of water in the modified organopolysiloxane solution is preferably 100 mg/kg or less, more preferably 90 mg/kg or less and still more preferably 60 mg/kg or less. On the other hand, from the viewpoint of a high efficiency of operation, the concentration of water in the modified organopolysiloxane solution is preferably 3 mg/kg or more, more preferably 5 mg/kg or more, still more preferably 10 mg/kg or more, and further still more preferably 30 mg/kg or more.

When the amount of water contained in the modified organopolysiloxane solution is excessively large, the solution is preferably subjected to dehydration and drying treatment. The dehydration and drying treatment may be carried out by the same method as used for dehydrating the cyclic iminoether compound solution in the step (a). More specifically, from the viewpoint of reducing a burden on facilities, the dehydration and drying treatment is more preferably carried out using a dehydration agent. As the dehydration agent, a molecular sieve is preferably used from the viewpoints of achievability of the water concentration and economy. From the viewpoint of shortening the dehydration time, the dehydration temperature is preferably 40° C. or lower. Also, from the viewpoint of a high efficiency of operation, the dehydration temperature is preferably 5° C. or higher. The dehydration agent may be directly added to the modified organopolysiloxane solution, followed by stirring the resulting mixture, and thereafter the dehydration agent may be removed from the mixture. However, from the viewpoint of a facilitated operation, the modified organopolysiloxane solution is preferably dehydrated and dried by passing through a column filled with the dehydration agent.

In a preferred embodiment of the present invention, from the viewpoint of well controlling a molecular weight of the resulting polymer, before initiating the next step (c), the terminal-reactive poly(N-acylalkylene imine) solution is preferably cooled. The terminal-reactive poly(N-acylalkylene imine) solution is preferably cooled to a temperature of 70° C. or lower, more preferably from 10 to 60° C., still more preferably from 20 to 60° C. and especially preferably from 25 to 40° C.

[Step (c)]

In the step (c), the terminal-reactive poly(N-acylalkylene imine) solution obtained in the step (a) and the modified organopolysiloxane solution obtained in the step (b) are mixed with each other to react an amino group contained in the modified organopolysiloxane with the terminal-reactive poly(N-acylalkylene imine).

(Bonding Reaction)

The temperature used in the reaction between the terminal-reactive poly(N-acylalkylene imine) solution and the modified organopolysiloxane solution is preferably from 40 to 150° C., more preferably from 60 to 120° C., still more preferably from 70 to 110° C. and further still more preferably from 75 to 100° C. From the viewpoint of well controlling a molecular weight of the resulting reaction product, the reaction temperature is preferably adjusted to the above-specified range after mixing the terminal-reactive poly(N-acylalkylene imine) solution and the modified organopolysiloxane solution with each other.

The reaction time may vary depending upon the reaction conditions such as polymerization temperature, and is usually from 1 to 60 h, preferably from 3 to 30 h and more preferably from 5 to 15 h.

The concentration of water in the reaction mixture obtained after mixing and reacting the terminal-reactive poly(N-acylalkylene imine) solution and the modified organopolysiloxane solution with each other is preferably controlled to 150 mg/kg or less, more preferably 120 mg/kg or less, still more preferably 100 mg/kg or less and further still more preferably 80 mg/kg or less by controlling the concentration of water in each of the terminal-reactive poly(N-acylalkylene imine) solution and the modified organopolysiloxane solution. The lower limit of the water concentration in the reaction mixture may be 0 mg/kg or more. From the viewpoint of a high efficiency of operation in the steps (a) and (b), the lower limit of the water concentration in the reaction mixture is preferably 5 mg/kg or more, more preferably 10 mg/kg or more, and still more preferably 30 mg/kg or more.

[Step (d)]

In the step (d), a basic substance is added to a reaction product obtained in the step (c).

By adding the basic substance to the reaction product in the step (d), it is possible to suppress reduction in molecular weight of the organopolysiloxane as the aimed product when removing the solvents therefrom under high-temperature conditions in the subsequent step (e).

From the viewpoint of suppressing reduction in molecular weight of the organopolysiloxane, the basic substance may be either an inorganic basic substance or an organic basic substance. Examples of the inorganic basic substance include alkali metal hydroxides, alkali earth metal hydroxides, alkali metal carbonates, alkali earth metal carbonates and alkali metal hydrogen carbonates. Among these inorganic basic substances, preferred are alkali metal hydroxides, and more preferred are sodium hydroxide, potassium hydroxide, etc.

Examples of the organic basic substance include amines containing a hydrocarbon group which may be substituted with a hydroxyl group.

From the viewpoint of a good solubility of the organopolysiloxane compound obtained by the method of the present invention in a solvent contained in products when compounded in the products, the basic substance is preferably the organic basic substance, and more preferably an amine containing a hydrocarbon group which may be substituted with a hydroxyl group. Specific examples of the amine containing a hydrocarbon group which may be substituted with a hydroxyl group include monomethylamine, dimethylamine, monoethanolamine, ethylenediamine, N-methylethanolamine, monoisopropanolamine, methoxypropylamine, aminoethylethanolamine, 2-amino-2-methyl-1-propanol (hereinafter occasionally referred to merely as "AMP"), 2-amino-2-methyl-1,3-propanediol, 2-amino-1-butanol, diethanolamine (hereinafter occasionally referred to merely as "DEA"), diethylenetriamine, N-acetylethanolamine, dimethylaminopropylamine, 2-amino-2-ethyl-1,3-propanediol, 3-dimethylaminopropylamine, triethylamine, triethanolamine, triethylenediamine, hexamethylenediamine, diisopropanolamine, m-phenylenediamine, toluene-2,5-diamine, dibutylamine, 2-ethylhexylamine, N,N-dimethylcyclohexylamine, triisopropanolamine, benzyldimethylamine, m-xylenediamine, tributylamine, tetradecylamine, dimethyllaurylamine, di-2-ethylhexylamine and dimethylstearamine.

Among these amines containing a hydrocarbon group which may be substituted with a hydroxyl group, preferred are amines having a total carbon number of 6 or less from the viewpoint of a good solubility of the organopolysiloxane compound obtained by the method of the present invention in a solvent contained in products when compounded in the products, in particular, a solubility thereof in a polar solvent such as water and ethanol, and preferred are amines having a total carbon number of 2 or more from the viewpoint of a boiling point and easiness in handling upon production thereof. Further, from the viewpoint of a good solubility in the solvent contained in the products and a boiling point, the organic basic substance is preferably an amine containing a hydrocarbon group which is substituted with a hydroxyl group.

Therefore, among the above amines, from the viewpoint of a good solubility in the solvent contained in the above products and a boiling point, preferred are dimethylamine, monoethanolamine, ethylenediamine, N-methylethanolamine, monoisopropanolamine, methoxypropylamine, aminoethylethanolamine, AMP, 2-amino-2-methyl-1,3-propanediol, 2-amino-1-butanol, DEA, diethylenetriamine, N-acetylethanolamine, dimethylaminopropylamine, 2-amino-2-ethyl-1,3-propanediol, 3-dimethylaminopropylamine, triethylamine, triethanolamine, triethylenediamine, hexamethylenediamine and diisopropanolamine, and more preferred are monoethanolamine, N-methylethanolamine, monoisopropanolamine, aminoethylethanolamine, AMP, 2-amino-2-methyl-1,3-propanediol, 2-amino-1-butanol, DEA, N-acetylethanolamine, 2-amino-2-ethyl-1,3-propanediol, triethanolamine and diisopropanolamine. From the viewpoints of a good availability and low costs, still more preferred are AMP and DEA.

These basic substances may be used alone or in combination of any two or more thereof.

The basic substance is preferably used in an amount of from 10 to 500 mol %, more preferably from 10 to 100 mol % and still more preferably from 10 to 30 mol % on the basis of the polymerization initiator used from the viewpoint of suppressing reduction in molecular weight of the aimed product.

[Step (e)]

In the step (e), the solvents are removed from a mixture obtained after the addition in the step (d) at a temperature of from 100 to 200° C.

When using the organopolysiloxane compound as the aimed product in personal care product application fields, the odor of solvents is not desirable. Therefore, it is desired to remove residual solvents from the products and reduce them to as small a level as possible. The removal of the solvents from the reaction solution is preferably conducted at a temperature of from 120 to 170° C. and more preferably from 140 to 160° C. From the viewpoint of efficiently removing the solvents, the removal procedure is preferably carried out under reduced pressure.

The concentration of the residual solvents in the reaction solution is preferably 3000 mg/kg or less, more preferably 2000 mg/kg or less and especially preferably 1000 mg/kg or less from the viewpoint of efficiently removing the odor of the residual solvents.

In a preferred embodiment of the present invention, from the viewpoint of a good production efficiency, the solvents may be removed using a solvent removal apparatus having a twin screw as described in JP 10-279690A. The solvent removal apparatus has a space extending from a vessel bottom to an upper end of the twin screw as an effective capacity. On an upper portion of the effective capacity, as an evaporation chamber, there is present a uniform space extending from a raw material feed port to a dried product discharge port. On a ceiling portion of the evaporation chamber, there is provided a vent hole connected to a reduced pressure line.

The removal of the solvents is preferably carried out in an inert gas atmosphere such as nitrogen from the viewpoint of suppressing coloration of the resulting modified organopolysiloxane.

EXAMPLES (Measurement of Average Value of Mass Ratio of Organopolysiloxane Segment)

In the following Examples and Comparative Examples, the average value of a mass ratio of the organopolysiloxane segment was determined as follows. That is, the organopolysiloxane compound according to the present invention was dissolved in deuterated chloroform to prepare a 5% by mass chloroform solution of the organopolysiloxane compound. The thus prepared solution was then subjected to nuclear magnetic resonance ($^1$H-NMR) analysis using the following measuring apparatus to thereby determine an integral ratio between an alkyl group or a phenyl group in the organopolysiloxane segment and a methylene group in the poly(N-acylalkylene imine) segment. The mass ratio of the organopolysiloxane segment was calculated from the integral ratio.

<Measuring Apparatus>

Apparatus:

"Varian Mercury 400BB" (400 MHz) available from Varian Inc.

Measuring Mode:

Relax. delay=10 sec

Pulse=45 degrees

Acquisition time=3.28 sec

Repetitions=8 times (Measurement of Molecular Weight)

The number-average molecular weight of the terminal-reactive poly(N-propionylethylene imine) and the weight-average molecular weight of the organopolysiloxane compound were measured by gel permeation chromatography (GPC) under the following conditions.

Measuring Conditions

Column: "K-804L" (tradename; available from Showa Denko K.K.); two columns connected in series were used.

Eluent: 1 mmol/L of "Farmin DM20" (tradename; available from Kao Corp.)/chloroform Flow Rate: 1.0 mL/min Column Temperature: 40° C.

Detector: Differential Refractometer

Sample: 5 mg/mL; 100 μL

The molecular weight was measured in terms of a polystyrene as a reference standard substance.

In the following Examples and Comparative Examples, the molecular weight of the organopolysiloxane segment was substantially the same as the weight-average molecular weight of the side-chain primary aminopropyl-modified organopolysiloxane. The weight-average molecular weight of the side-chain primary aminopropyl-modified organopolysiloxane was determined by acetylating the side-chain primary aminopropyl-modified organopolysiloxane by the following method and then subjecting the resulting acetylated product to GPC under the same measuring conditions as used for measurement of the weight-average molecular weight of the above (N-propionylethylene imine).

<Acetylation of Side-Chain Primary Aminopropyl-Modified Organopolysiloxane>

The round bottom flask equipped with a cooling tube was charged with 90 g of chloroform and 10 g of the side-chain primary aminopropyl-modified poly(dimethyl siloxane), and the contents of the flask were uniformly dissolved. Next, acetic anhydride was added to the flask in an equivalent amount based on an amino group of the side-chain primary aminopropyl-modified poly(dimethyl siloxane), and the contents of the flask were stirred under reflux for 8 h to subject the amino group to acetylation. After allowing the resulting product to stand for cooling, the solvent was removed therefrom under reduced pressure to prepare a sample for measurement of a molecular weight thereof.

(Measurement of Water Concentration)

The concentration of water in the resulting solution was measured using the following apparatus.

Apparatus: Karl Fischer Moisture Meter "CA-06" (tradename) available from Mitsubishi Chemical Corp.

Reagent on cathode side: "AQUAMICRON CK" (tradename) available from Mitsubishi Chemical Corp.

Reagent on anode side: "AQUAMICRON AU" (tradename) available from Mitsubishi Chemical Corp.: "AQUAMICRON CM" (tradename) available from Mitsubishi Chemical Corp.=20:80 (% by volume)

(Measurement of Amount of Unreacted Amine)

The sample was accurately weighed in an amount of 3 g, and dissolved in a mixed solvent containing methanol and chloroform at a volume ratio (methanol/chloroform) of 50/50. The resulting solution was subjected to titration with a 0.1 mol/L perchloric acid/acetic acid standard solution using a potentiometric titration apparatus. At the same time, a blank test of the above procedure was carried out. From the measured values, the amine value was calculated according to the following calculation formula.

$$\text{Amine Value (mol/g)} = (A-B) \times f / (\text{amount of sample (g)} \times 10000)$$

wherein A represents an amount (mL) of a 0.1 mol/L perchloric acid/acetic acid standard solution used for titration of the sample; B represents an amount (mL) of a 0.1 mol/L perchloric acid/acetic acid standard solution used in the black test; and f represents a factor of the 0.1 mol/L perchloric acid/acetic acid standard solution.

(Evaluation of Solubility in Polar Solvent)

The solubility of the organopolysiloxane compound obtained by the method of the present invention in a polar solvent was evaluated as follows. That is, the resulting organopolysiloxane compound was dispersed or dissolved in ethanol to prepare a dispersion or a solution thereof, and the resulting dispersion or solution was subjected to measurement of a light transmittance thereof ($\lambda$=650 nm) to evaluate a solubility thereof in ethanol.

More specifically, the organopolysiloxane compound (after dried) obtained in each of Examples and Comparative Examples was accurately weighed in an amount of 1.0 g, and added to 9.0 g of ethanol to prepare a dispersion or solution thereof. The resulting 10 mass % dispersion or solution of the organopolysiloxane compound was measured for light transmittance at 650 nm under the following conditions. In this case, it is meant that the higher the light transmittance, the more excellent the solubility in ethanol becomes.

Measuring Apparatus: Ultraviolet-Visible Spectrophotometer "UV-2550" (tradename) available from Shimadzu Corporation.
Cell: Quartz cell (optical path length: 1 cm)
Measuring wavelength: 650 nm Example 1

(Step (a))

A mixed solution prepared by mixing 59.0 g (0.60 mol) of 2-ethyl-2-oxazoline and 143.3 g of ethyl acetate was dehydrated with 10.1 g of a molecular sieve ("ZEOLUM A-4" (tradename) available from Tosoh Corporation) for 15 h to reduce a water concentration of the solution to 100 mg/kg or less.

The resulting dehydrated ethyl acetate solution of 2-ethyl-2-oxazoline was mixed with 11.56 g (0.075 mol) of diethyl sulfate, and the obtained mixture was refluxed under heating at 80° C. in a nitrogen atmosphere for 8 h, thereby synthesizing terminal-reactive poly(N-propionylethylene imine). As a result of subjecting the resulting reaction product to GPC, it was confirmed that the number-average molecular weight thereof was 900.

(Step (b))

A mixed solution prepared by mixing 150.0 g (amino group content: 0.075 mol) of a side-chain primary aminopropyl-modified poly(dimethyl siloxane) ("KF-8003" (tradename) available from Shin-Etsu Chemical Co., Ltd.; weight-average molecular weight: 50,000; amine equivalent: 2,000) and 304.2 g of ethyl acetate was dehydrated with 23 g of the molecular sieve for 15 h to reduce a water concentration of the solution to 100 mg/kg or less.

(Step (c))

The terminal-reactive poly(N-propionylethylene imine) solution obtained in the step (a) was cooled to 30° C., and then the dehydrated side-chain primary aminopropyl-modified poly(dimethyl siloxane) solution obtained in the step was added thereto at one time. The resulting mixture was refluxed under heating at 80° C. for 10 h and then cooled, thereby obtaining 660 g of an ethyl acetate solution of an N-propionylethylene imine-dimethyl siloxane copolymer (the organopolysiloxane compound according to the present invention) (hereinafter occasionally referred to merely as a "solution (1)"). A part of the resulting solution was concentrated under reduced pressure at room temperature to obtain the organopolysiloxane compound in the form of a light yellow solid. The average value of a mass ratio of the organopolysiloxane segment was 0.67, and the weight-average molecular weight of the resulting organopolysiloxane compound was 85,000. As a result of subjecting the resulting organopolysiloxane compound to neutralization titration, it was confirmed that no amino group remained therein.

(Steps (d) and (e))

Fifty grams of the solution (1) obtained in the step (c) (including 0.0056 mol of diethyl sulfate as a polymerization initiator) were mixed with 120 mg (0.0013 mol; 23 mol % based on the polymerization initiator) of 2-amino-2-methyl-1-propanol (AMP) to prepare a uniform solution, and then the resulting solution was charged into a flat stainless steel vat and dried therein at 150° C. under reduced pressure (10 kPa) for 1 h. As a result of subjecting the resulting solid to GPC, it was confirmed that the solid had a weight-average molecular weight of 85,000.

Comparative Example 1

Fifty grams of the solution (1) obtained in the step (c) in Example 1 was charged into a flat stainless steel vat and then dried therein at 150° C. under reduced pressure for 1 h. As a result, it was confirmed that the obtained solid had a weight-average molecular weight of 66,000.

TABLE 1

|  |  | Example 1 | Comparative Example 1 |
|---|---|---|---|
| Raw material before drying | Kind of solution | Solution (1) | Solution (1) |
|  | Weight-average molecular weight | 85,000 | 85,000 |
|  | Amount used (g) | 50 | 50 |
| Basic substance | Kind | AMP | — |
|  | Amount added (mg) | 120 | — |
|  | (mol %*) | (23) |  |
| Drying treatment | Temperature (° C.) | 150 | 150 |
|  | Time (h) | 1 | 1 |
| After drying | Weight-average molecular weight | 85,000 | 66,000 |

Note:
*Mol % based on the polymerization initiator contained in the solution (1)
AMP: 2-Amino-2-methyl-1-propanol As apparently recognized from the results shown in Table 1, the organopolysiloxane compound obtained in Comparative Example 1 in which no basic substance was added suffered from reduction in molecular weight thereof owing to heating upon the drying treatment for removal of the solvent. The reduced molecular weight of the organopolysiloxane compound resulted in occurrence of stickiness and therefore poor touch. On the other hand, the organopolysiloxane compound obtained in Example 1 in which the basic substance was added was free from reduction in molecular weight even when heated upon the drying treatment.

Example 2

(Step (a))

A mixed solution prepared by mixing 68.4 g (0.69 mol) of 2-ethyl-2-oxazoline and 164.0 g of ethyl acetate was dehydrated with 11.6 g of a molecular sieve ("ZEOLUM A-4" (tradename) available from Tosoh Corporation) for 15 h to reduce a water concentration of the solution to 100 mg/kg or less.

The resulting dehydrated ethyl acetate solution of 2-ethyl-2-oxazoline was mixed with 12.4 g (0.080 mol) of diethyl sulfate, and the obtained mixture was refluxed under heating at 80° C. in a nitrogen atmosphere for 8 h, thereby synthesizing terminal-reactive poly(N-propionylethylene imine). As a result of subjecting the resulting product to GPC, it was confirmed that the number-average molecular weight thereof was 1,000.

(Step (b))

A mixed solution prepared by mixing 150.0 g (amino group content: 0.080 mol) of a side-chain primary aminopropyl-modified poly(dimethyl siloxane) ("KF-8003" (tradename) available from Shin-Etsu Chemical Co., Ltd.; weight-average molecular weight: 50,000; amine equivalent: 1870) and 304.5 g of ethyl acetate was dehydrated with 22.7 g of the molecular sieve for 15 h to reduce a water concentration of the solution to 100 mg/kg or less.

(Step (c))

The terminal-reactive poly(N-propionylethylene imine) solution obtained in the step (a) was cooled to 30° C., and then the dehydrated side-chain primary aminopropyl-modified poly(dimethyl siloxane) solution obtained in the step was added thereto at one time. The resulting mixture was refluxed under heating at 80° C. for 10 h and then cooled, thereby obtaining 695 g of an ethyl acetate solution of an N-propionylethylene imine-dimethyl siloxane copolymer (the organopolysiloxane compound according to the present invention) (hereinafter occasionally referred to merely as a "solution (2)"). A part of the resulting solution was concentrated under reduced pressure at room temperature to obtain the organopolysiloxane compound in the form of a light yellow solid. The average value of a mass ratio of the organopolysiloxane segment was 0.65, and the weight-average molecular weight of the resulting organopolysiloxane compound was 50,000. As a result of subjecting the resulting organopolysiloxane compound to neutralization titration, it was confirmed that no amino group remained therein.

(Steps (d) and (e))

Thirty (30.0) grams of the solution (2) obtained in the step (c) (including 0.0034 mol of diethyl sulfate as a polymerization initiator) were mixed with 31 mg (0.00034 mol; 10 mol % based on the polymerization initiator) of AMP to prepare a uniform solution, and then the resulting solution was charged into a flat stainless steel vat and dried therein at 150° C. under reduced pressure (10 kPa) for 1 h. As a result of subjecting the resulting solid to GPC, it was confirmed that the solid had a weight-average molecular weight of 38,000. Also, it was confirmed that the resulting product had a light transmittance of 98%.

Examples 3 to 5

The same procedure as in Example 2 was repeated except that the amount of AMP added was changed as shown in Table 2. The measurement results of a weight-average molecular weight and a light transmittance of the solid obtained after drying are shown together in Table 2.

Examples 6 to 9

The same procedure as in Example 2 was repeated except that diethanol amine (DEA) was used as the basic substance, and the amount of the basic substance added was changed as shown in Table 2. The measurement results of a weight-average molecular weight and a light transmittance of the solid obtained after drying are shown together in Table 2.

Examples 10 to 13

The same procedure as in Example 2 was repeated except that a 20 mass % potassium hydroxide ethanol solution was used as the basic substance, and the amount of the basic substance added was changed as shown in Table 2. The measurement results of a weight-average molecular weight and a light transmittance of the solid obtained after drying are shown together in Table 2.

Comparative Example 2

The same procedure as in Example 2 was repeated except that no basic substance was added. As a result, it was confirmed that the solid obtained after drying had a weight-average molecular weight of 23000 and a light transmittance of 96%. The results are shown in Table 2.

TABLE 2

| | | Examples | | | | | | | |
|---|---|---|---|---|---|---|---|---|---|
| | | 2 | 3 | 4 | 5 | 6 | 7 | 8 | 9 |
| Raw material before drying | Kind of solution | Solution (2) | Solution (2) | Solution (2) | Solution (2) | Solution (2) | Solution (2) | Solution (2) | Solution (2) |
| | Weight-average molecular weight | 50,000 | 50,000 | 50,000 | 50,000 | 50,000 | 50,000 | 50,000 | 50,000 |
| | Amount used (g) | 30 | 30 | 30 | 30 | 30 | 30 | 30 | 30 |
| Basic substance | Kind | AMP | AMP | AMP | AMP | DEA | DEA | DEA | DEA |
| | Amount added (mg) | 31 | 77 | 153 | 307 | 36 | 90 | 181 | 362 |
| | (mol %*) | (10) | (25) | (50) | (100) | (10) | (25) | (50) | (100) |
| Drying treatment | Temperature (° C.) | 150 | 150 | 150 | 150 | 150 | 150 | 150 | 150 |
| | Time (h) | 1 | 1 | 1 | 1 | 1 | 1 | 1 | 1 |
| After drying | Weight-average molecular weight | 38,000 | 51,000 | 51,000 | 50,000 | 44,000 | 45,000 | 47,000 | 50,000 |
| | Light transmittance (%)** | 98 | 99 | 99 | 99 | 99 | 99 | 99 | 99 |

| | | Examples | | | | Comparative |
|---|---|---|---|---|---|---|
| | | 10 | 11 | 12 | 13 | Example 2 |
| Raw material before drying | Kind of solution | Solution (2) | Solution (2) | Solution (2) | Solution (2) | Solution (2) |
| | Weight-average molecular weight | 50,000 | 50,000 | 50,000 | 50,000 | 50,000 |
| | Amount used (g) | 30 | 30 | 30 | 30 | 30 |

TABLE 2-continued

| Basic substance | Kind | KOH/Et | KOH/Et | KOH/Et | KOH/Et | — |
|---|---|---|---|---|---|---|
| | Amount added (mg) | 97*** | 241*** | 483*** | 965*** | — |
| | (mol %*) | (10) | (25) | (50) | (100) | |
| Drying treatment | Temperature (° C.) | 150 | 150 | 150 | 150 | 150 |
| | Time (h) | 1 | 1 | 1 | 1 | 1 |
| After drying | Weight-average molecular weight | 30,000 | 39,000 | 59,000 | 63,000 | 23,000 |
| | Light transmittance (%)** | 64 | 70 | 78 | 73 | 96 |

Note:
*Mol % based on the polymerization initiator contained in the solution (2)
**Light transmittance of 10% dispersion or solution (solvent: ethanol) as measured at a wavelength of 650 nm
***The amount added was an amount of a 20 mass % potassium hydroxide ethanol solution added.
AMP: 2-Amino-2methyl-1-propanol
DEA: Diethanol amine
KOH/Et: A 20 mass % potassium hydroxide ethanol solution

INDUSTRIAL APPLICABILITY

The organopolysiloxane compound produced according to the present invention can be inhibited from suffering from reduction in molecular weight, can exhibit a good touch without stickiness, and can be suitably used as a base material for cosmetics.

The invention claimed is:

1. A method, comprising:
(a) subjecting a cyclic iminoether compound represented by general formula (I):

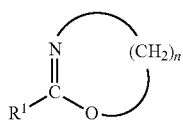

to ring opening polymerization in a solvent to prepare a solution of a terminal-reactive poly(N-acylalkylene imine), wherein
$R^1$ is a hydrogen atom, an alkyl group having 1 to 22 carbon atoms, an aralkyl group or an aryl group, and n is a number of 2 or 3;
(b) mixing a modified organopolysiloxane comprising an amino group bonded to a terminal end, to a side chain, or to a terminal end and a side chain of a molecular chain thereof with a solvent to prepare a solution of the modified organopolysiloxane;
(c) mixing the terminal-reactive poly(N-acylalkylene imine) solution obtained from said subjecting with the modified organopolysiloxane solution obtained from said (b) mixing to react the amino group of the modified organopolysiloxane with the terminal-reactive poly(N-acylalkylene imine);
(d) adding a basic substance to a reaction product obtained in said mixing (c) wherein the basic substance is at least one compound selected from the group consisting of an alkali metal hydroxide and an amine containing at least one hydrocarbon group substituted with a hydroxyl group; and
(e) removing the solvents from a mixture obtained after the addition in said adding (d) at a temperature of from 100 to 200° C.,
thereby obtaining an organopolysiloxane compound having a structure in which a poly(N-acylalkylene imine) segment comprising a repeating unit represented by general formula (1):

is bonded to a terminal end, a side chain, or a terminal end and a side chain of an organopolysiloxane segment, wherein $R^1$ is a hydrogen atom, an alkyl group having 1 to 22 carbon atoms, an aralkyl group or an aryl group, and n is a number of 2 or 3.

2. The method according to claim 1, wherein the basic substance is at least one compound selected from the group consisting of sodium hydroxide, potassium hydroxide, a trialkanolamine and 2-amino-2-methyl-1-propanol.

3. The method according to claim 1, wherein the ring opening polymerization of said subjecting is carried out in the presence of a polymerization initiator.

4. The method according to claim 3, wherein the polymerization initiator is selected from the group consisting of a benzene-sulfonic acid alkyl ester, an acid alkyl ester, a p-toluene-sulfonic acid alkyl ester, a trifluoromethane-sulfonic acid alkyl ester, a trifluoroacetic acid alkyl ester, and a sulfuric acid dialkyl ester.

5. The method according to claim 3, wherein the polymerization initiator is a dialkyl sulfate comprising an alkyl group having 1 to 3 carbon atoms.

6. The method according to claim 3, wherein the polymerization initiator is present in an amount of 1 mol on the basis of from 2 to 100 mol of the cyclic iminoether compound.

7. The method according to claim 1, wherein the basic substance is an amine comprising a hydrocarbon group which may be substituted with a hydroxyl group.

8. The method according to claim 7, wherein the amine comprising the hydrocarbon group which may be substituted with the hydroxyl group is an amine having a total carbon number of from 2 to 6.

9. The method according to claim 3, wherein the basic substance is present in an amount of from 10 to 500 mol % on the basis of the polymerization initiator.

10. The method according to claim 1, wherein the solvent present during said subjecting is an aprotic polar solvent.

11. The method according to claim 1, wherein the solvent present during said subjecting is selected from the group consisting of an acetic acid C1 to C3 alkyl ester; a C1 to C3 dialkyl ether; a cyclic ether; a ketone; a halogen solvent; a nitrile solvent; N,N-dimethylformamide; N,N-dimethylacetamide; and dimethyl sulfoxide.

12. The method according to claim 1, wherein the concentration of water present in the cyclic iminoether compound solution prepared by mixing the cyclic iminoether compound in the solvent is from 10 mg/kg to 600 mg/kg.

13. The method according to claim 1, wherein the cyclic iminoether compound solution prepared by mixing the cyclic iminoether compound in the solvent is subjected to dehydration and drying treatment.

14. The method according to claim 13, wherein the dehydration and drying treatment is carried out with a dehydration agent.

15. The method according to claim 14, wherein the dehydration agent is selected from the group consisting of a molecular sieve, alumina, calcium chloride, and calcium sulfate.

* * * * *